United States Patent
Rudolph

(10) Patent No.: US 10,791,780 B2
(45) Date of Patent: *Oct. 6, 2020

(54) PROTECTIVE GLOVES WITH IMPROVED FINGERTIP FITMENT AND METHODS AND MOLD-FORMS FOR MANUFACTURING SUCH GLOVES

(71) Applicant: Ross Rudolph, La Jolla, CA (US)

(72) Inventor: Ross Rudolph, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/566,796

(22) Filed: Sep. 10, 2019

(65) Prior Publication Data

US 2020/0000161 A1  Jan. 2, 2020

Related U.S. Application Data

(63) Continuation of application No. 16/364,008, filed on Mar. 25, 2019, now Pat. No. 10,413,004, which is a continuation of application No. 16/228,531, filed on Dec. 20, 2018, now abandoned, which is a continuation-in-part of application No. 15/967,864, filed on May 1, 2018, now abandoned.

(51) Int. Cl.
| | |
|---|---|
| *A41D 19/00* | (2006.01) |
| *A61B 42/10* | (2016.01) |
| *A41D 19/04* | (2006.01) |
| *B29C 41/40* | (2006.01) |
| *B29L 31/48* | (2006.01) |

(52) U.S. Cl.
CPC ......... *A41D 19/04* (2013.01); *A41D 19/0058* (2013.01); *A61B 42/10* (2016.02); *B29C 41/40* (2013.01); *A41D 2600/20* (2013.01); *B29L 2031/4864* (2013.01)

(58) Field of Classification Search
None
See application file for complete search history.

(56) References Cited

U.S. PATENT DOCUMENTS

| | | |
|---|---|---|
| 1,369,341 A | 2/1921 | Kearns |
| 2,462,239 A | 2/1949 | Van Dinter et al. |
| 2,538,160 A | 1/1951 | Milton, Jr. et al. |
| 2,581,248 A | 1/1952 | Ganz |
| 2,605,548 A | 8/1952 | Clarke |
| 2,753,593 A | 7/1956 | Duff |
| 3,013,302 A | 12/1961 | Croxton |
| 3,148,235 A | 9/1964 | Velonis et al. |
| 3,170,194 A | 2/1965 | Abildgaard |
| 3,255,492 A | 6/1966 | Velonis et al. |
| 3,286,011 A | 11/1966 | Kavalir et al. |

(Continued)

OTHER PUBLICATIONS

Brock, "Gloves for Small Hands (Where to buy small sized gloves)", https://www.themodestman.com/gloves-for-small-hands/, 15 pages. (Year: 2017).*

(Continued)

*Primary Examiner* — Xiao S Zhao
*Assistant Examiner* — Emmanuel S Luk
(74) *Attorney, Agent, or Firm* — Procopio Cory Hargreaves and Savitch LLP

(57) ABSTRACT

A surgical glove mold set, comprising a plurality of surgical glove mold-forms, wherein each surgical glove mold-form of the plurality of surgical glove mold-forms includes a common palm width (PW) and different finger lengths.

5 Claims, 4 Drawing Sheets

(56) References Cited

U.S. PATENT DOCUMENTS

| | | |
|---|---|---|
| 3,487,146 A | 12/1969 | Tillotson |
| 3,843,296 A | 10/1974 | Sidley |
| 3,852,826 A | 12/1974 | Schindler |
| 3,975,776 A | 8/1976 | Ayres |
| 4,018,382 A | 4/1977 | DiCuya |
| 4,047,251 A | 9/1977 | Stockum |
| 4,115,873 A | 9/1978 | Stansbury |
| 4,135,867 A | 1/1979 | Stockum |
| 4,189,787 A | 2/1980 | Stansbury |
| 4,218,778 A | 8/1980 | Stansbury |
| 4,340,348 A | 7/1982 | Kurtz |
| 4,390,492 A | 6/1983 | Kurtz |
| 4,521,365 A | 6/1985 | Kurtz |
| 4,696,065 A | 9/1987 | Elenteny |
| 4,921,672 A | 5/1990 | Bock |
| 5,234,141 A | 8/1993 | Spiece |
| 5,249,234 A | 9/1993 | Butler |
| D347,312 S | 5/1994 | Spiece |
| 5,345,612 A | 9/1994 | Stein |
| 5,644,797 A | 7/1997 | Daneshvar |
| 5,776,520 A | 7/1998 | Howe et al. |
| 5,833,911 A | 11/1998 | Llort et al. |
| 5,907,870 A | 6/1999 | Monroe et al. |
| 5,926,888 A | 7/1999 | Chen et al. |
| 6,415,446 B1 | 7/2002 | McLean et al. |
| 6,760,923 B1 | 7/2004 | Tate |
| 7,159,246 B2 | 1/2007 | Tippey |
| D655,878 S | 3/2012 | Hajduk |
| 8,495,764 B2 | 7/2013 | Hull |
| 8,512,615 B1 | 8/2013 | Amdur et al. |
| 8,578,519 B2 | 11/2013 | Kantrowitz et al. |
| 8,856,967 B2 | 10/2014 | Govindasamy et al. |
| 8,985,469 B2 | 3/2015 | Coombes |
| 9,179,718 B2 | 11/2015 | Anstey |
| 9,370,209 B2 | 6/2016 | Hull |
| 9,414,630 B2 | 8/2016 | Schatzberg et al. |
| 10,085,499 B2 | 10/2018 | Hao |
| D839,487 S | 1/2019 | Pu |
| 2003/0124354 A1 | 7/2003 | Vistins |
| 2005/0274750 A1 | 12/2005 | Cho |
| 2006/0041991 A1 | 3/2006 | Kim Sim |
| 2010/0325778 A1 | 12/2010 | Cunningham |
| 2011/0191936 A1 | 8/2011 | Lipinski et al. |
| 2014/0150162 A1 | 6/2014 | Guan |
| 2014/0208480 A1 | 7/2014 | Champagne et al. |
| 2016/0050993 A1 | 2/2016 | Sood |

OTHER PUBLICATIONS

Havas, "Your Glove Size", https://www.glove.org/Modern/glovemeasure.php., 3 pages. (Year: 2018).*

"5 Good Glove Fit Factors", Hourglass International Inc, https://hourglass-inl.com/2014/03/11/5-good-glove-fit-factors/, 5 pages. (Year: 2014).*

"Safety Glove Size Chart", Grainger Industrial Supply, https://www.grainger.com/content/qt-safety-glove-size-chart-306, 3 pages. (Year: 2015).*

* cited by examiner

PROTECTIVE GLOVES WITH IMPROVED FINGERTIP FITMENT AND METHODS AND MOLD-FORMS FOR MANUFACTURING SUCH GLOVES

CROSS-REFERENCE TO RELATED APPLICATION

This application is a continuation of U.S. patent application Ser. No. 16/364,008, filed Mar. 25, 2019, which is a continuation of U.S. patent application Ser. No. 16/228,531, filed Dec. 20, 2018, which is a continuation-in-part of U.S. patent application Ser. No. 15/967,864, filed on May 1, 2018, which are incorporated by reference herein.

BACKGROUND

1. Field of the Invention

The present disclosure is related to protective gloves that have improved fingertip fitment. More particularly, the present disclosure is related to gloves and methods and mold-forms for manufacturing such gloves.

2. Description of Related Art

Protective gloves (hereinafter "gloves") are ubiquitous in medical care and other commercial or non-commercial fields. In the medical field, the gloves are used for sterility and/or protection of the practitioner and/or patient. In other fields, the gloves are used for cleanliness and/or protection of the user and/or the workpiece being contacted by the user. These other fields can include, but are not limited to, manufacturing, assembly, maintenance, art, crafts, and others.

In many instances, the gloves must fit precisely, as meticulous procedures like surgery are done while the gloves are being worn. Thus, exact fit on the practitioner's hands is essential. Of particular importance are the fingertip areas, which are essential to precision tactile sensitivity.

Ill-fitting gloves can impair manual dexterity, can increase discomfort during extended use, and have other deleterious effects. Gloves that are too tight in any aspect (e.g., palm width, finger length, or others) cause hand fatigue and other symptoms related to compression at the wrist. Conversely, gloves that are too loose can get in the way of the task being performed by the practitioner.

In some fields involving human blood practitioners often "double glove" where a second pair of gloves is worn over a first pair of gloves. The practice of double gloving can provide added protection against contamination, needle sticks, and the like, as well as for other benefits. However, the second pair of gloves can exacerbate any attributes of an ill-fitting first pair of gloves.

Many prior art gloves are provided in numerical sizes. The numerical glove size is traditionally indicative of a measurement of the palm circumference, in inches. For example, some common sizes are 6, 6½, 7, 7½, 8, 8½, and 9.

The palm width in centimeters is generally a measure of the dominant hand—where the width is measured across the palm of the hand, but excludes the thumb. Palm circumference and palm width are directly related.

In the prior art, the palm width is then used to set the proportions of other aspects of the gloves—such as finger length. Finger length, similar to palm width, is a measure of the dominant hand—where the length is measured from the tip to the base of the finger. Simply stated, the prior art gloves set the finger length based on the palm width so that a certain size glove always gives a certain standard finger length.

Gloves have been made traditionally from latex-based rubber. Because of increasing allergic problems to latex, gloves are now being made of other types of plastic materials in increasing numbers. The elastic nature of these materials has been thought to be helpful at overcoming differences in hand sizes.

However, it has been determined by the present disclosure that measurement system used by prior art gloves—based on palm width and standard finger lengths to that palm width—and regardless of the materials used have proven insufficient for many practitioners, because of lack of precise fingertip fit.

Accordingly, there is a need for gloves and methods and mold-forms for manufacturing such gloves that overcome, alleviate, and/or mitigate one or more of the aforementioned and other deleterious effects of the prior art.

SUMMARY

The present disclosure for glove mold-forms provides gloves having three different ratios of finger length to palm width that provide improved precision in the fitting of the glove fingertips. Specifically, the gloves of the present application are provided using the numerical sizes, but where each size has three different finger length designations—short, medium, and long. Methods and mold-forms for manufacturing such gloves are provided.

Another aspect of the invention involves a surgical glove mold set, comprising a plurality of surgical glove mold-forms, wherein each surgical glove mold-form of the plurality of surgical glove mold-forms includes a common palm width (PW) and different finger lengths.

An implementation of the aspect of the invention described immediately above includes that the plurality of surgical glove mold-forms have three surgical glove mold-forms representing short, medium, and long finger lengths, respectively.

A further aspect of the invention involves a method of manufacturing surgical gloves comprising selecting a particular mold-form from a plurality of mold-forms, where the plurality of mold-forms have the same palm width (PW) and have different finger lengths; providing a film material to a desired thickness on the particular mold-form; solidifying the film on the particular mold-form; removing the film from the particular mold-form to provide a surgical glove of the desired palm width and finger length.

One or more implementations of the aspect of the invention described immediately above include one or more of the following: providing the film with a glove donning assisting agent on an interior of the glove; the glove donning assisting agent comprises at least one of a powder and a surface modifier; the glove donning assisting agent comprises chlorination or polymer modification or other agents, and any combinations thereof; the glove donning assisting agent comprises a surface modifier selected from the group consisting of a chemical treatment, a halogenation, a hydrogel polymer, and any combinations thereof; indicating on at least one of glove and a package into which the glove is placed a marking that indicates the palm width of the mold-form and a finger length designation; providing the selected particular mold-form with a releasing agent configured to assist in releasing the film from the particular mold-form; providing step comprises providing the film as one or more layers; the film providing step comprises a process selected from the group consisting of dipping, spraying, evaporating, printing, and any combinations thereof; and/or the film solidification step comprises solidifying the film by a process selected from the group consisting of drying, curing, cooling, crosslinking, and any combinations thereof, followed by sterilization.

A still further aspect of the invention involves a kit of surgical gloves comprising a first plurality of surgical gloves; and a second plurality of surgical gloves, the surgical gloves in the first and second pluralities having the same palm width and different finger lengths.

One or more implementations of the aspect of the invention described immediately above include one or more of the following: a third plurality of surgical gloves, the surgical gloves in the third plurality having the same palm width as the first and second pluralities but different finger lengths from the first and second pluralities; and/or a package having the first and second pluralities of surgical gloves separately stored therein.

The above-described and other features and advantages of the present disclosure will be appreciated and understood by those skilled in the art from the following detailed description, drawings, and appended claims.

DETAILED DESCRIPTION

Figure 1:
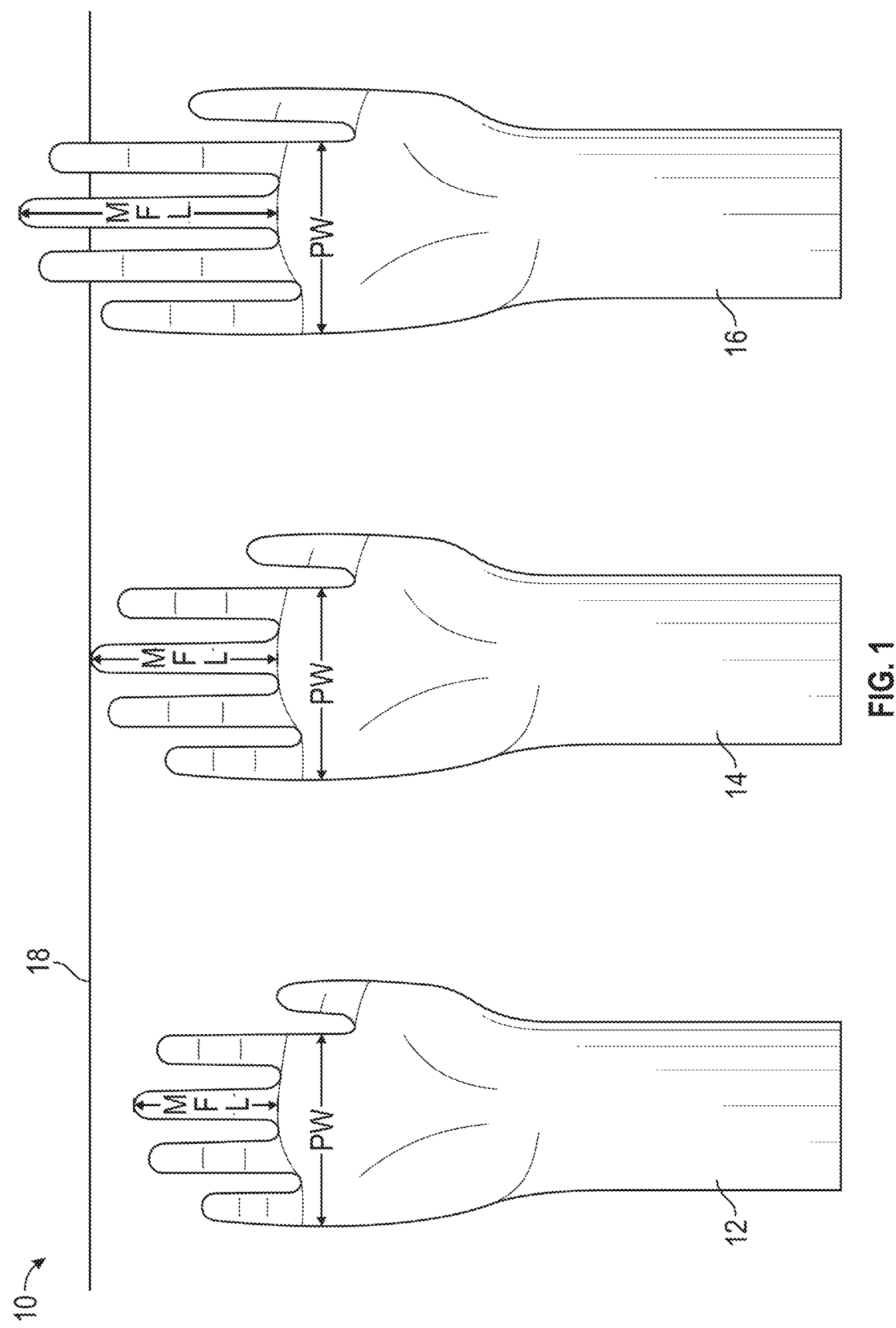
FIG. 1 is a schematic depiction of a set of glove mold-forms according to an exemplary embodiment of the present disclosure.

Referring to the drawings and in particular to FIG. 1, a set of mold-forms for manufacturing sterile surgical gloves according to the present disclosure are shown and are generally referred to by reference numeral 10. In alternative embodiments, other types of gloves (e.g., non-sterile examination gloves) are manufactured with the system(s) and method(s) shown and/or described herein.

Advantageously and as described in more detail below, set 10 includes three mold-forms 12, 14, 16, respectively— where all three of the molds have the same numeric size and palm width (PW), but have a different finger length— illustrated as the middle finger length (MFL). Mold-forms 12, 14, 16 are shown for clarity of discussion as a mold for a right hand palm side only. However, it should be recognized that set 10 includes mold-forms 12, 14, 16 for both hands.

In the illustrated embodiment, set 10 includes mold-form 12 having the shortest finger length, mold-form 14 having a medium finger length, and mold-form 16 having a longest finger length. For clarity, set 10 is illustrated having a comparison line 18 that uses mold-form 14 as the base line finger length to compare the finger lengths of mold-forms 12, 16.

It has been determined by the present disclosure that not all hands have the same proportions. Some practitioners have a large palm width with short fingers, while others have a small palm width with long fingers. It has been determined that the current manufacturing techniques do not provide sufficient precision due to variability in hand anthropometry. In contrast, set 10 allows the easy manufacture of gloves having the desired ratio of finger length to palm width (PW).

Figure 2:
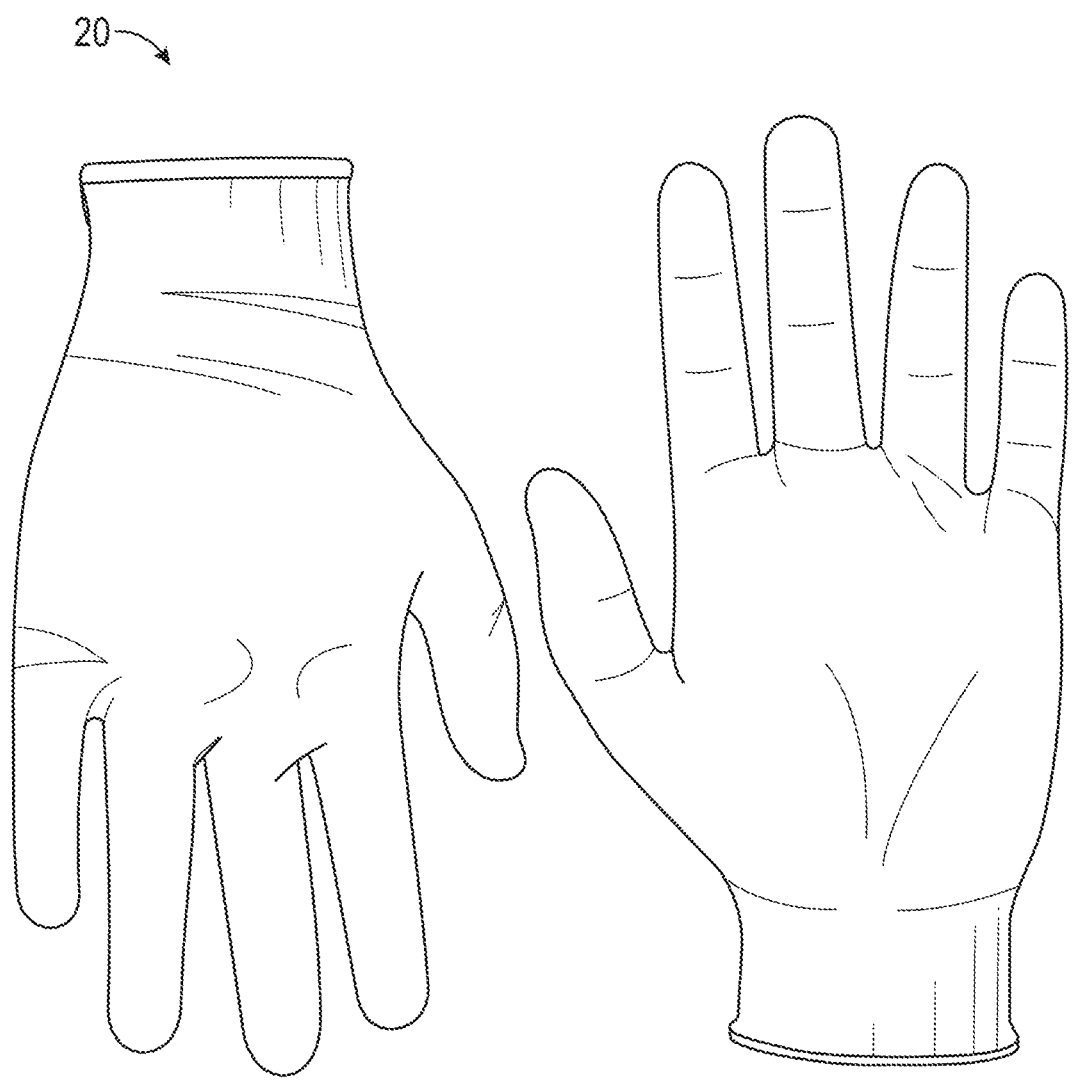
FIG. 2 illustrates an exemplary embodiment of a glove produced from a mold-form according to the present disclosure.

Thus, each mold-form 12, 14, 16 allows the manufacture of a pair of gloves 20—one pair shown in FIG. 2—that is easily marked or sold by numerical size, with the palm width (PW) as in the prior art, but allows greater selection by further indicating finger length from among three easy to select sizes—short, medium, and long.

Since prior art mold-forms for glove manufacture were not readily available for measurement, TABLE 1 below provides exemplary measurements of prior art gloves to provide an understanding of the ratio of finger length (base of finger to tip) to palm width commercially available.

TABLE 1

|  | Size 6½ | Size 7½ |
| --- | --- | --- |
| Palm Width (PW) | 7.1 cm | 8.4 cm |
| Thumb Length (TL) | 5.5 cm | 5.7 cm |
| Ratio TL to PW | .77:1 | .68:1 |
| Index Finger Length (IFL) | 6.1 cm | 6.4 cm |
| Ratio IFL to PW | .86:1 | .76:1 |
| Middle Finger Length (MFL) | 7.1 cm | 7.8 cm |
| Ratio MFL to PW | 1:1 | .93:1 |
| Ring Finger Length (RFL) | 6.6 cm | 7.3 cm |
| Ratio RFL to PW | .93:1 | .87:1 |
| Little Finger Length (LFL) | 5.3 cm | 5.6 cm |
| Ratio LFL to PW | .75:1 | .67:1 |
| Average ratio of finger length (FL) to palm width (PW) | .86:1 | .78:1 |

From TABLE 1, it can be determined that the average ratio of finger length—for all five fingers—to palm width for the two gloves sizes 6½ and 7½ removed from packaging is either 0.86:1 or 0.78:1—with different palm widths. Thus, the prior art gloves provide a solution for selection of the gloves that forces the user to select based on palm width or based on finger length. Although the data of TABLE 1 is based on measurement of the prior art gloves and, not the mold-forms used to make those gloves, this data provides an understanding of the different finger length to palm width ratios available from the prior art.

In contrast, gloves 20 made using set 10 of mold-forms 12, 14, 16, provides the practitioner with multiple choices of finger length for each palm width, which correct the glaring lack of precision available from prior art gloves. Moreover, set 10 allows gloves 20 to be sized using the current long-established numeric system of glove selection, but with a simple indicator of finger length—short, medium, and long. In alternative embodiments, the multiple choices of finger length for each palm width may be other than short, medium, long. For example, but not by way of limitation, the multiple choices may be one or more of S-Small, M-Medium, L-Large, XL-Extra Large, and/or XXL-Extra Extra Large.

TABLES 2-8 below provide exemplary dimensions of seven different sets (glove sizes 6, 6½, 7, 7½, 8, 8½ and 9) 10 of mold-forms 12, 14, 16 to provide an understanding of the ratio of finger length to palm width of the present application. Manufacturing will be of all glove sizes 6, 6½, 7, 7½, 8, 8½ and 9.

TABLE 2

| | first plurality of surgical gloves | | |
|---|---|---|---|
| | Size 6 Short (12) | Size 6 Medium (14) | Size 6 Long (16) |
| Palm Width (PW) | 7.5 cm | 7.5 cm | 7.5 cm |
| Thumb Length (TL) | 5.1 cm | 5.5 cm | 6.0 cm |
| Ratio TL to PW | .68:1 | .73:1 | .80:1 |
| Index Finger Length (IFL) | 5.8 cm | 6.2 cm | 6.7 cm |
| Ratio IFL to PW | .77:1 | .83:1 | .89:1 |
| Middle Finger Length (MFL) | 6.6 cm | 7.2 cm | 7.7 cm |
| Ratio MFL to PW | .88:1 | .96:1 | 1.03:1 |
| Ring Finger Length (RFL) | 6.4 cm | 6.8 cm | 7.3 cm |
| Ratio RFL to PW | .85:1 | .91:1 | .97:1 |
| Little Finger Length (LFL) | 4.8 cm | 5.2 cm | 5.7 cm |
| Ratio LFL to PW | .64:1 | .69:1 | .76:1 |
| Average ratio of finger length (FL) to palm width (PW) | .76:1 | .82:1 | .89:1 |

TABLE 3

| | second plurality of surgical gloves | | |
|---|---|---|---|
| | Size 6½ - Short (12) | Size 6½ - Medium (14) | Size 6½ - Long (16) |
| Palm Width (PW) | 7.75 cm | 7.75 cm | 7.75 cm |
| Thumb Length (TL) | 5.8 cm | 6.2 cm | 6.6 cm |
| Ratio TL to PW | .75:1 | .80:1 | .85:1 |
| Index Finger Length (IFL) | 6.3 cm | 6.7 cm | 7.1 cm |
| Ratio IFL to PW | .81:1 | .86:1 | .92:1 |
| Middle Finger Length (MFL) | 7.2 cm | 7.6 cm | 8.0 cm |
| Ratio MFL to PW | .92:1 | .98:1 | 1.03:1 |
| Ring Finger Length (RFL) | 6.9 cm | 7.1 cm | 7.5 cm |
| Ratio RFL to PW | .89:1 | .92;1 | .97:1 |
| Little Finger Length (LFL) | 5.4 cm | 5.8 cm | 6.2 cm |
| Ratio LFL to PW | .70:1 | .75:1 | .80:1 |
| Average ratio of finger length (FL) to palm width (PW) | .81:1 | .86:1 | .91:1 |

TABLE 4

| | third plurality of surgical gloves | | |
|---|---|---|---|
| | Size 7 - Short (12) | Size 7 - Medium (14) | Size 7 - Long (16) |
| Palm Width (PW) | 8.4 cm | 8.4 cm | 8.4 cm |
| Thumb Length (TL) | 6.0 cm | 6.4 cm | 7.0 cm |
| Ratio TL to PW | .71:1 | .76:1 | .83:1 |
| Index Finger Length (IFL) | 6.5 cm | 7.0 cm | 7.5 cm |
| Ratio IFL to PW | .77:1 | .83:1 | .89:1 |
| Middle Finger Length (MFL) | 7.3 cm | 7.9 cm | 8.4 cm |
| Ratio MFL to PW | .87:1 | .94:1 | 1:1 |
| Ring Finger Length (RFL) | 7.1 cm | 7.4 cm | 7.9 cm |
| Ratio RFL to PW | .85:1 | .88:1 | .94:1 |
| Little Finger Length (LFL) | 5.6 cm | 5.9 cm | 6.4 cm |
| Ratio LFL to PW | .67:1 | .70:1 | .76:1 |
| Average ratio of finger length (FL) to palm width (PW) | .77:1 | .82:1 | .88:1 |

TABLE 5

| | fourth plurality of surgical gloves | | |
|---|---|---|---|
| | Size 7½ - Short (12) | Size 7½ - Medium (14) | Size 7½ - Long (16) |
| Palm Width (PW) | 8.75 cm | 8.75 cm | 8.75 cm |
| Thumb Length (TL) | 6.2 cm | 6.8 cm | 7.3 cm |
| Ratio TL to PW | .71:1 | .78:1 | .83:1 |
| Index Finger Length (IFL) | 6.7 cm | 7.2 cm | 7.6 cm |
| Ratio IFL to PW | .76:1 | .82:1 | .87:1 |
| Middle Finger Length (MFL) | 7.5 cm | 8.1 cm | 8.6 cm |
| Ratio MFL to PW | .86:1 | .93:1 | .98:1 |
| Ring Finger Length (RFL) | 7.0 cm | 7.6 cm | 8.1 cm |
| Ratio RFL to PW | .80:1 | .87:1 | .93:1 |
| Little Finger Length (LFL) | 5.5 cm | 6.1 cm | 6.6 cm |
| Ratio LFL to PW | .63:1 | .70:1 | .75:1 |
| Average ratio of finger length (FL) to palm width (PW) | .75:1 | .82:1 | .87:1 |

TABLE 6

| | fifth plurality of surgical gloves | | |
|---|---|---|---|
| | Size 8 Short (12) | Size 8 Medium (14) | Size 8 Long (16) |
| Palm Width (PW) | 8.9 cm | 8.9 cm | 8.9 cm |
| Thumb Length (TL) | 6.3 cm | 7.0 cm | 7.5 cm |
| Ratio TL to PW | .71:1 | .79:1 | .84:1 |
| Index Finger Length (IFL) | 7.2 cm | 7.5 cm | 8.3 cm |
| Ratio IFL to PW | .81:1 | .89:1 | .93:1 |
| Middle Finger Length (MFL) | 7.8 cm | 8.4 cm | 8.9 cm |
| Ratio MFL to PW | .88:1 | .94:1 | 1:1 |
| Ring Finger Length (RFL) | 7.5 cm | 8.1 cm | 8.6 cm |
| Ratio RFL to PW | .84:1 | .91:1 | .97:1 |
| Little Finger Length (LFL) | 5.8 cm | 6.6 cm | 7.2 cm |
| Ratio LFL to PW | .65:1 | .74:1 | .81:1 |
| Average ratio of finger length (FL) to palm width (PW) | .78:1 | .85:1 | .91:1 |

TABLE 7

| | sixth plurality of surgical gloves | | |
|---|---|---|---|
| | Size 8½ Short (12) | Size 8½ Medium (14) | Size 8½ Long (16) |
| Palm Width (PW) | 9.6 cm | 9.6 cm | 9.6 cm |
| Thumb Length (TL) | 6.8 cm | 7.5 cm | 7.9 cm |
| Ratio TL to PW | .71:1 | .78:1 | .82:1 |
| Index Finger Length (IFL) | 7.4 cm | 8.1 cm | 8.5 cm |
| Ratio IFL to PW | .77:1 | .84:1 | .89:1 |
| Middle Finger Length (MFL) | 8.1 cm | 8.8 cm | 9.3 cm |
| Ratio MFL to PW | .84:1 | .92:1 | .97:1 |
| Ring Finger Length (RFL) | 7.8 cm | 8.5 cm | 8.9cm |
| Ratio RFL to PW | .81:1 | .89:1 | .93:1 |
| Little Finger Length (LFL) | 6.2 cm | 7.1 cm | 7.5 cm |
| Ratio LFL to PW | .65:1 | .74:1 | .78:1 |
| Average ratio of finger length (FL) to palm width (PW) | .76:1 | .83:1 | .88:1 |

TABLE 8

| | seventh plurality of surgical gloves | | |
|---|---|---|---|
| | Size 9 Short (12) | Size 9 Medium (14) | Size 9 Long (16) |
| Palm Width (PW) | 10.5 cm | 10.5 cm | 10.5 cm |
| Thumb Length (TL) | 7.1 cm | 7.7 cm | 8.4 cm |
| Ratio TL to PW | .68:1 | .73:1 | .80:1 |
| Index Finger Length (IFL) | 7.6 cm | 8.3 cm | 8.8 cm |
| Ratio IFL to PW | .72:1 | .79:1 | .84:1 |
| Middle Finger Length (MFL) | 8.5 cm | 9.0 cm | 9.5 cm |
| Ratio MFL to PW | .82:1 | .86:1 | .90:1 |
| Ring Finger Length (RFL) | 8.2 cm | 8.6 cm | 9.3 cm |
| Ratio RFL to PW | .78:1 | .82:1 | .89:1 |
| Little Finger Length (LFL) | 6.5 cm | 7.3 cm | 7.8 cm |

TABLE 8-continued

| | seventh plurality of surgical gloves | | |
|---|---|---|---|
| | Size 9 Short (12) | Size 9 Medium (14) | Size 9 Long (16) |
| Ratio LFL to PW | .62:1 | .70:1 | .74:1 |
| Average ratio of finger length (FL) to palm width (PW) | .72:1 | .78:1 | .83:1 |

From the data of TABLES 2-8, it can be seen that the practitioners can—for each palm width—select from three different average ratios of finger length to palm width, which provides much greater flexibility to optimize the glove 20 to their hand.

Figure 3:
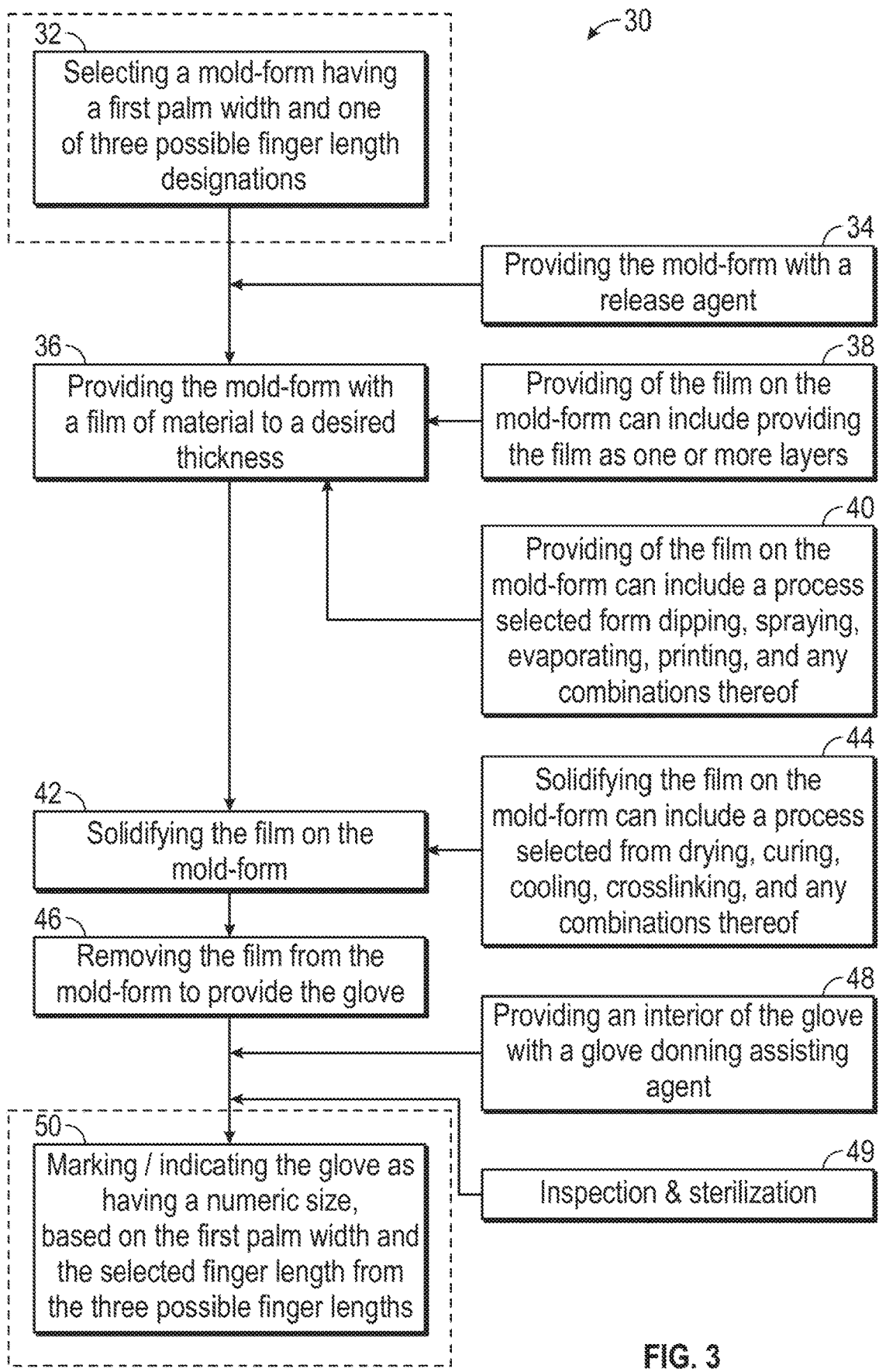
FIG. 3 illustrates an exemplary embodiment of a method of manufacturing gloves using the set of mold-forms of FIG. 1.

Referring now to FIG. 3, a method of manufacturing gloves 20 using set 10 of mold-forms 12, 14, 16 according to the present disclosure is shown and is generally referred to by reference numeral 30.

Method 30 includes a mold-form selection step 32. Here, the manufacturer selects a set 10 of mold-forms 12, 14, 16 that have a first palm width (PW) and selects a particular mold-form that has one of three possible finger length designations (e.g., short, medium, or long).

In some embodiments, method 30 can include a releasing agent providing step 34. Here, method 30 provides the selected mold-form with a releasing agent configured to assist in releasing the film applied by film providing step 36 from the mold-form.

Method 30 includes a film providing step 36. Here, the selected mold-is provided form with a film of material to a desired thickness.

The film providing step 36 can, in some embodiments, include providing the film as one or more layers as shown in step 38. The film providing step 36 can, in some embodiments, include providing the film by any desired process such as, but not limited to, dipping, spraying, evaporating, printing, and any combinations thereof as shown in step 40.

Method 30 includes a film solidification step 42 where the film is solidified on the mold-form. The film solidification step 42 can, in some embodiments, include solidifying the film by a process such as, but not limited to, drying, curing, cooling, crosslinking, and any combinations thereof as shown in step 44.

Method 30 includes a film removal step 46 where the film is removed from the mold-form to provide glove 20 of the desired palm width and finger length.

Method 30 can, in some embodiments, include providing the film with a glove donning assisting agent as shown in step 48. During step 48, the interior of the glove is provided with a glove donning assisting agent that assists a practitioner in donning the glove. The agent can include, but is not limited to, a surface modifier. The surface modifiers can include chemical treatment such as halogenation, hydrogel polymer, and others.

It should be recognized that step 48 is shown by way of example as being after step 46. Of course, it is contemplated by the present disclosure for the assisting agent to be applied at any desired point in method 30. Moreover, it is contemplated by the present disclosure for the releasing agent of step 36 and the assisting agent of step 48 to be the same material and/or applied during the same step.

During step 49, multiple stages of inspection and sterilization and packaging complete the manufacturing process.

Method 30 can include a glove size marking/indicating step 50. During step 50, the glove and/or the package into which the glove is placed can be marked to indicate the palm width of the mold-form—preferably in a numeral manner and to indicate the finger length of the mold-form, preferably using a designation of the three finger lengths in the set 10 relative to one another (e.g., short, medium, or long). Thus, step 50 indicates the glove as having a size based on the palm width and the selected finger length of from the three possible finger lengths.

Figure 4:
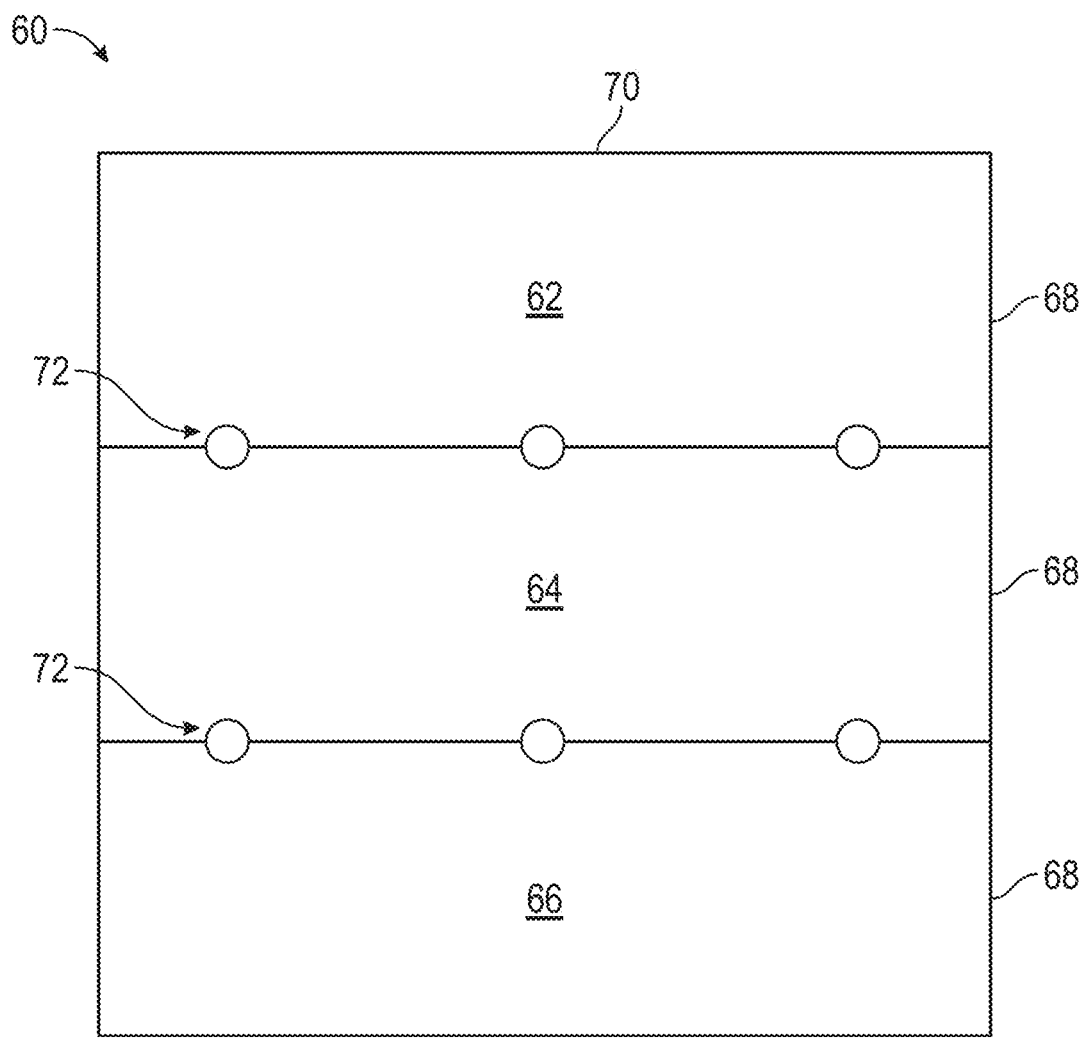
FIG. 4 is a kit of gloves made using the set of mold-forms of FIG. 1.

Referring now to FIG. 4, a kit of gloves made using the set of mold-forms of FIG. 1 is shown and is generally referred to by reference numeral 60. Kit 60 includes a first plurality of gloves 62, a second plurality of gloves 64, and, in some embodiments, a third plurality of gloves 66. Advantageously, all of the gloves 62, 64, 66 have the same palm width (PW), but the first plurality 62 has a short finger length, the second plurality 64 has a medium finger length, and the third plurality 66 has a long finger length.

Kit 60 can be formed by at least two separate packages 68 that are connected to one another by, for example a wrapping 70 and/or adhesives 72. Alternately, kit 60 can be a single unitary package 68 divided into at least two sections each having a different plurality of gloves 62, 64, 66.

In use, practitioners can easily select a pair of gloves 20 based on their known palm width using the conventional numeric glove sizing indicators, combined with a finger length from three possible finger lengths—short, medium, and long.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed:

1. A method of manufacturing disposable surgical gloves, comprising:
    selecting a particular disposable surgical glove mold-form from a plurality of disposable surgical glove mold-forms, where the plurality of disposable surgical glove mold-forms have a common palm width (PW) and have different finger lengths compared to respective finger lengths of a standard medium-sized disposable surgical glove mold-form of the plurality of disposable surgical glove mold-forms having a common palm width (PW);
    providing a film material to a desired thickness on the particular disposable surgical glove mold-form;
    solidifying the film on the particular disposable surgical glove mold-form;
    removing the film from the particular disposable surgical glove mold-form to provide a disposable surgical glove of a desired palm width and finger length,
    wherein particular disposable surgical glove mold-form includes a ratio of thumb length (TL) to palm width (PW) that is one of: more than 0.73:1 for a 7.5 cm palm width (PW), more than 0.80:1 for a 7.75 cm palm width (PW), more than 0.76:1 for an 8.4 cm palm width (PW), more than 0.78:1 for an 8.75 cm palm width (PW), more than 0.79:1 for an 8.9 cm palm width (PW), more than 0.78:1 for a 9.6 cm palm width (PW), more than 0.73:1 for a 10.5 cm palm width (PW).

2. A method of manufacturing disposable surgical gloves, comprising:

selecting a particular disposable surgical glove mold-form from a plurality of disposable surgical glove mold-forms, where the plurality of disposable surgical glove mold-forms have a common palm width (PW) and have different finger lengths compared to respective finger lengths of a standard medium-sized disposable surgical glove mold-form of the plurality of disposable surgical glove mold-forms having a common palm width (PW);

providing a film material to a desired thickness on the particular disposable surgical glove mold-form;

solidifying the film on the particular disposable surgical glove mold-form;

removing the film from the particular disposable surgical glove mold-form to provide a disposable surgical glove of a desired palm width and finger length, wherein particular disposable surgical glove mold-form includes a ratio of Index Finger Length (IFL) to palm width (PW) that is one of: more than 0.83:1 for a 7.5 cm palm width (PW), more than 0.86:1 for a 7.75 cm palm width (PW), more than 0.83:1 for an 8.4 cm palm width (PW), more than 0.82:1 for an 8.75 cm palm width (PW), more than 0.89:1 for an 8.9 cm palm width (PW), more than 0.84:1 for a 9.6 cm palm width (PW), more than 0.79:1 for a 10.5 cm palm width (PW).

3. A method of manufacturing disposable surgical gloves, comprising:

selecting a particular disposable surgical glove mold-form from a plurality of disposable surgical glove mold-forms, where the plurality of disposable surgical glove mold-forms have a common palm width (PW) and have different finger lengths compared to respective finger lengths of a standard medium-sized disposable surgical glove mold-form of the plurality of disposable surgical glove mold-forms having a common palm width (PW);

providing a film material to a desired thickness on the particular disposable surgical glove mold-form;

solidifying the film on the particular disposable surgical glove mold-form;

removing the film from the particular disposable surgical glove mold-form to provide a disposable surgical glove of a desired palm width and finger length, wherein particular disposable surgical glove mold-form includes a ratio of Middle Finger Length (MFL) to palm width (PW) that is one of: more than 0.96:1 for a 7.5 cm palm width (PW), more than 0.98:1 for a 7.75 cm palm width (PW), more than 0.94:1 for an 8.4 cm palm width (PW), more than 0.93:1 for an 8.75 cm palm width (PW), more than 0.94:1 for an 8.9 cm palm width (PW), more than 0.92:1 for a 9.6 cm palm width (PW), more than 0.86:1 for a 10.5 cm palm width (PW).

4. A method of manufacturing disposable surgical gloves, comprising:

selecting a particular disposable surgical glove mold-form from a plurality of disposable surgical glove mold-forms, where the plurality of disposable surgical glove mold-forms have a common palm width (PW) and have different finger lengths compared to respective finger lengths of a standard medium-sized disposable surgical glove mold-form of the plurality of disposable surgical glove mold-forms having a common palm width (PW);

providing a film material to a desired thickness on the particular disposable surgical glove mold-form;

solidifying the film on the particular disposable surgical glove mold-form;

removing the film from the particular disposable surgical glove mold-form to provide a disposable surgical glove of a desired palm width and finger length, wherein particular disposable surgical glove mold-form includes a ratio of Ring Finger Length (RFL) to palm width (PW) that is one of: more than 0.91:1 for a 7.5 cm palm width (PW), more than 0.92:1 for a 7.75 cm palm width (PW), more than 0.88:1 for an 8.4 cm palm width (PW), more than 0.87:1 for an 8.75 cm palm width (PW), more than 0.91:1 for an 8.9 cm palm width (PW), more than 0.89:1 for a 9.6 cm palm width (PW), more than 0.82:1 for a 10.5 cm palm width (PW).

5. A method of manufacturing disposable surgical gloves, comprising:

selecting a particular disposable surgical glove mold-form from a plurality of disposable surgical glove mold-forms, where the plurality of disposable surgical glove mold-forms have a common palm width (PW) and have different finger lengths compared to respective finger lengths of a standard medium-sized disposable surgical glove mold-form of the plurality of disposable surgical glove mold-forms having a common palm width (PW);

providing a film material to a desired thickness on the particular disposable surgical glove mold-form;

solidifying the film on the particular disposable surgical glove mold-form;

removing the film from the particular disposable surgical glove mold-form to provide a disposable surgical glove of a desired palm width and finger length, wherein particular disposable surgical glove mold-form includes a ratio of Little Finger Length (LFL) to palm width (PW) that is one of: more than 0.69:1 for a 7.5 cm palm width (PW), more than 0.75:1 for a 7.75 cm palm width (PW), more than 0.70:1 for an 8.4 cm palm width (PW), more than 0.71:1 for an 8.75 cm palm width (PW), more than 0.74:1 for an 8.9 cm palm width (PW), more than 0.74:1 for a 9.6 cm palm width (PW), more than 0.70:1 for a 10.5 cm palm width (PW).

\* \* \* \* \*